(12) United States Patent
Kurek et al.

(10) Patent No.: US 6,395,942 B1
(45) Date of Patent: *May 28, 2002

(54) INCREASING THE THERMAL STABILITY OF A VINYL AROMATIC POLYMERIZATION INHIBITOR

(75) Inventors: Paul R. Kurek, Barrington; Robert R. Frame, Glenview, both of IL (US)

(73) Assignee: UOP LLC, Des Plaines, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/371,349

(22) Filed: Aug. 10, 1999

(51) Int. Cl.⁷ .................................................. C07C 7/20
(52) U.S. Cl. ............................. 585/5; 585/832; 585/4; 208/2; 208/48 AA; 208/348; 208/349
(58) Field of Search ................................ 585/4, 5, 832; 208/2, 48 AA, 348, 349

(56) References Cited

U.S. PATENT DOCUMENTS

| | | | | |
|---|---|---|---|---|
| 3,988,212 A | | 10/1976 | Watson ........................ 203/209 |
| 4,013,580 A | | 3/1977 | Hayashi et al. ............... 252/182 |
| 4,050,993 A | | 9/1977 | Daniels ........................ 203/209 |
| 4,341,600 A | | 7/1982 | Watson ........................ 203/209 |
| 4,466,905 A | * | 8/1984 | Butler et al. ................. 252/403 |
| 4,654,451 A | | 3/1987 | Miller et al. ................. 585/585 |
| 4,774,374 A | * | 9/1988 | Abruscato et al. ............ 585/24 |
| 4,863,587 A | * | 9/1989 | Tonari et al. ................ 208/263 |
| 4,929,778 A | | 5/1990 | Roling ........................ 585/583 |
| 4,967,027 A | | 10/1990 | Takahashi et al. ........... 585/585 |
| 4,973,787 A | * | 11/1990 | Colvin ........................ 585/508 |
| 4,982,034 A | * | 1/1991 | Moore et al. ................ 585/435 |
| 5,034,156 A | | 7/1991 | Varwig ........................ 252/403 |
| 5,254,760 A | | 10/1993 | Winter et al. ................ 585/585 |
| 5,312,952 A | | 5/1994 | Grossi et al. ................. 558/546 |
| 5,396,004 A | | 3/1995 | Arhancet et al. ............. 585/585 |
| 5,396,005 A | * | 3/1995 | Arhancet ........................ 585/5 |
| 5,446,220 A | * | 8/1995 | Arhancet ........................ 585/5 |
| 5,773,674 A | * | 6/1998 | Arhancet et al. ............... 585/5 |
| 5,869,717 A | * | 2/1999 | Frame et al. ................... 585/5 |
| 6,117,276 A | * | 9/2000 | Cunkle et al. .................. 203/8 |

FOREIGN PATENT DOCUMENTS

| | | |
|---|---|---|
| EP | 0 697 386 A1 | 7/1995 |
| JP | 59029624 A | 8/1982 |
| JP | 1226858 A | 9/1989 |
| JP | 3149205 A | 6/1991 |
| JP | 05310815 A | 11/1993 |
| JP | 07010910 A | 1/1995 |
| WO | WO95/03263 | 2/1995 |

* cited by examiner

*Primary Examiner*—Bekir L. Yildirim
(74) *Attorney, Agent, or Firm*—John G. Tolomei; Frank S. Molinaro

(57) ABSTRACT

Compounds that inhibit polymerization of vinyl aromatic compounds need to operate at temperatures of about 90° C. to about 150° C. A process for increasing the thermal stability of inhibitors such as N,N'-di-2-butyl-N,N'-dinitroso-1,4-diaminobenzene is disclosed. The process comprises adding to the inhibitor a stabilizer such as N,N'-di-2-butyl-1,4-diaminobenzene. The mixture of inhibitor and stabilizer is also used to inhibit polymerization of vinyl aromatic compounds.

13 Claims, No Drawings

INCREASING THE THERMAL STABILITY OF A VINYL AROMATIC POLYMERIZATION INHIBITOR

FIELD OF THE INVENTION

This invention relates to a process for increasing the thermal stability of a vinyl aromatic polymerization inhibitor by adding an inhibitor such as N,N'-di-2-butyl-N,N'-dinitroso-1,4-diaminobenzene to a stabilizer compound such as N,N'-di-2-butyl-1,4-diaminobenzene. The mixture of inhibitor and stabilizer can be used in a process for inhibiting the polymerization of vinyl aromatic compounds such as styrene during its distillation.

BACKGROUND OF THE INVENTION

Styrene is one of several vinyl aromatic compounds which has considerable commercial utility. Styrene is polymerized into polystyrene, which is a clear, readily colored and easily fabricated plastic with many uses. The efficiency of the polymerization process is dependent on the purity of the monomer starting material. Since the processes for producing styrene, and other vinyl aromatic compounds, will contain various reaction products including benzene, toluene, etc., the mixture is distilled to separate these undesirable contaminants. Unfortunately, the temperatures required for distillation, typically 90° C. to about 150° C., leads to the polymerization of the vinyl aromatic compounds. In order to minimize or prevent polymerization of the vinyl aromatic monomer, it is common to add a polymerization inhibitor to the distillation mixture.

The art discloses a variety of compounds, which are claimed to inhibit polymerization. These include U.S. Pat. No. 4,050,993, which discloses the use of N,N-nitrosomethylaniline as a polymerization inhibitor. U.S. Pat. No. 3,988,212 which disclose the use of N-nitrosodiphenyl amine in combination with dinitro-o-cresol. U.S. Pat. No. 4,013,580, which discloses the use of N-nitroso aniline derivatives. U.S. Pat. No. 4,341,600, which discloses the use of a mixture of dinitro-p-cresol and N-nitroso-diphenyl amine. U.S. Pat. No. 4,654,451, which discloses mixtures of alkyl substituted p-nitroso phenols and p-nitroso phenol. U.S. Pat. No. 5,034,156, which discloses N-nitrosophenylhydroxylamine plus hydroquinone monomethyl ether. U.S. Pat. No. 5,396,004, which discloses a phenylenediamine compound plus a hydroxyalkylhydroxyl-amine compound. U.S. Pat. No. 5,254,760, which discloses 1-oxyl-2,2,6,6-tetramethylpiperidine plus an aromatic nitro compound. U.S. Pat. No. 4,929,778, which discloses a phenylenediamine compound plus a hindered phenol compound. U.S. Pat. No. 5,312,952, which discloses the use of the reaction product of a $C_9$–$C_{20}$ alkyl phenol with sulfuric and nitric acid and optionally an aryl or alkyl-substituted phenylenediamine. WO9503263, which discloses 3,5-di-tert-butyl-4-hydroxy-N,N-dimethyl benzyl amine. EP-697386-A2, which discloses 4-acetylamino-2,2,6,6-tetramethyl piperidine N-oxyl in combination with 4-nitroso phenol. JP0701910-A which discloses phosphite compounds, nitrosoamine compounds or phenol compounds. JP05310815-A, which discloses the ammonium salt of N-nitrosophenyl hydroxylamine. JP03149205-A, which discloses nitrosophenols plus dicyclohexylammonium nitrate. J01226858-A, which discloses the use of substituted nitrosobenzene. U.S. Pat. No. 4,967,027, which discloses p-nitroso phenol plus p-t-butyl catechol. J59029624-A, which discloses the use of N-nitroso compound, e.g., N-nitroso-diphenylamine and a catechol, e.g., p-t-butylcatechol. Finally, U.S. Pat. No. 5,869,717, discloses the use of N-nitroso derivates of unsubstituted or dialkyl substituted phenylenediamine.

Applicants have now found that the thermal stability of the mono or di-nitroso compounds described in U.S. Pat. No. 5,869,717 can be increased by adding to the nitroso containing compound a stabilizer such as an unsubstituted or substituted phenylenediamine (diaminobenzene) or a substituted phenolic compound. The importance of this discovery is that it extends the temperature range over which the inhibitor can be used. This in turn means that the combination of inhibitor and stabilizer is able to withstand higher temperature disruptions or swings.

SUMMARY OF THE INVENTION

As stated, this invention relates to a process for increasing the thermal stability of various polymerization inhibitors and to a process for inhibiting the polymerization of a vinyl aromatic compound during its distillation. One embodiment of the invention is a process for increasing the thermal stability of a polymerization inhibitor selected from the group consisting of:

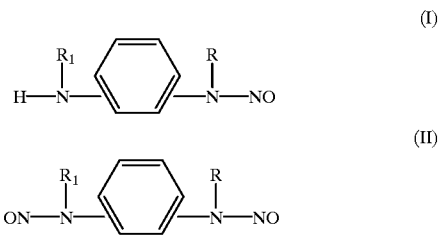

and mixtures thereof, where R and $R_1$ are each independently hydrogen, cyclohexyl, phenyl and an alkyl group having from 1 to 18 carbon atoms, the process comprising adding to the organic compound an effective amount of a stabilizer selected from the group consisting of:

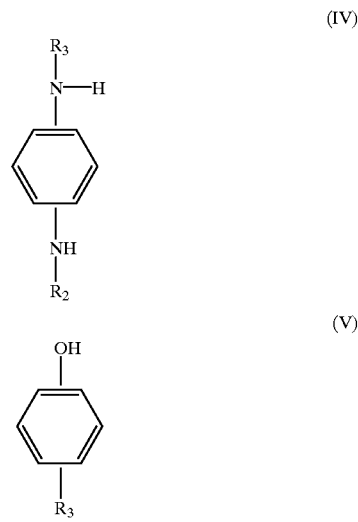

-continued

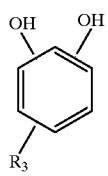
(VI)

and mixtures thereof, where $R_2$ is selected from the group consisting of hydrogen, phenyl, cyclohexyl and an alkyl group having from 1 to 18 carbon atoms, and $R_3$ is selected from the group consisting of hydrogen, an alkyl group having from 1 to 18 carbon atoms, cyclohexyl, and an aromatic group having from 6 to 10 carbon atoms.

Another embodiment of the invention is a process for inhibiting the polymerization of a vinyl aromatic compound during the distillation of the vinyl aromatic compound comprising adding to the compound an effective amount of a mixture of at least one polymerization inhibitor and at least one stabilizer, where the inhibitor is selected from the group consisting of:

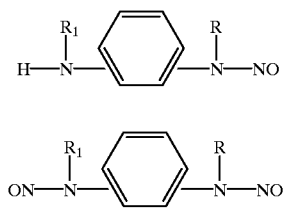
(I)

(II)

and mixtures thereof, where R and $R_1$ are each independently hydrogen, cyclohexyl, phenyl, or an alkyl group having from 1 to 18 carbon atoms, and the stabilizer is selected from the group consisting of:

(IV)

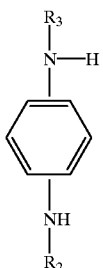

(V)

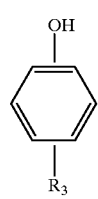

-continued

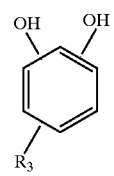
(VI)

and mixtures thereof, where $R_2$ is selected from the group consisting of hydrogen, cyclohexyl, phenyl, and an alkyl group having from 1 to 18 carbon atoms, and $R_3$ is selected from the group consisting of hydrogen, an alkyl group having from 1 to 18 carbon atoms, cyclohexyl, and an aromatic group having by from 6 to 10 carbon atoms.

These and other objects and embodiments will become more evident after a detailed description of the invention.

DETAILED DESCRIPTION OF THE INVENTION

The present invention relates to a process for increasing the thermal stability of a polymerization inhibitor and to a process for inhibiting the polymerization of a vinyl aromatic compound during its distillation. The polymerization inhibitors are selected from the group consisting of:

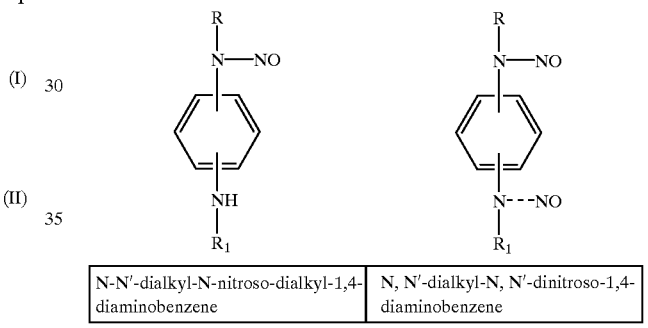

| N-N'-dialkyl-N-nitroso-dialkyl-1,4-diaminobenzene | N, N'-dialkyl-N, N'-dinitroso-1,4-diaminobenzene |

The R and $R_1$ groups can each independently be hydrogen or an alkyl group having from 1 to 18 carbon atoms. Illustrative of the alkyl groups which can be used are methyl, ethyl, propyl, butyl, pentyl, octyl, decyl, sec-butyl, isopropyl and isopentyl. Included in structures I and II above are the o, m and p isomers. Preferred compounds encompassed within structures I and II are the following compounds having structure IA and IIA.

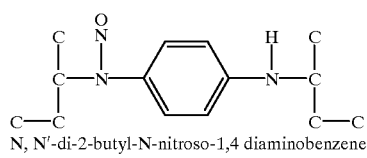
(I A)

N, N'-di-2-butyl-N-nitroso-1,4 diaminobenzene

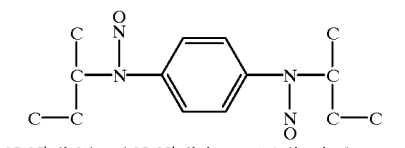
(IIA)

N, N'-di-2-butyl-N, N'-dinitroso-1,4-diaminobenzene

These nitroso compounds are prepared by reacting nitrous acid with an amine according to the procedure set forth in U.S. Pat. No. 5,869,717 which is incorporated by reference. The reaction of nitrous acid with an amine is well known in the art and is included here for completeness. Generally, the amine is reacted with nitrous acid at a temperature of about −10° C. to about 120° C. The nitrous acid can be added or it can be generated in situ by adding sodium nitrite and hydrochloric acid. Further, in the case of a diamine, the amount of nitrous acid added will determine whether the mono or dinitroso compounds are obtained. However, even if a 1:1 stoichiometric amount of nitrous acid:amine is added, a mixture of the mono and dinitroso compounds may still be obtained.

It has been found that the thermal stability of these polymerization inhibitors can be increased by adding to the inhibitor an effective amount of a stabilizer selected from the group consisting of:

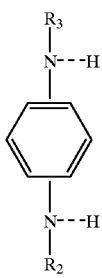

(IV)

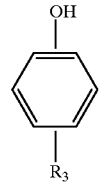

(V)

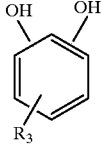

(VI)

and mixtures thereof and $R_2$ is selected from the group consisting of hydrogen, cyclohexyl, phenyl, and an alkyl group having from 1 to 18 carbon atoms, and $R_3$ is selected from the group consisting of hydrogen, an alkyl group having from 1 to 18 carbon atoms, cyclohexyl and an aromatic group having from 6 to 10 carbon atoms. Preferred stabilizers are those represented by structure (IV) and an especially preferred stabilizer has structure (IVA)

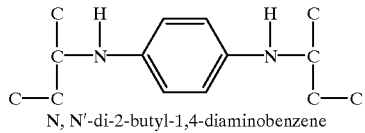

N, N'-di-2-butyl-1,4-diaminobenzene (IVA)

Of the various polymerization inhibitors, preferred ones are those having structure (II) and an especially preferred inhibitor is that having structure (IIA) an N,N'-dinitroso-N, N'-di-2-butyl-p-phenylenediamine. The amount of stabilizer necessary to increase the decomposition temperature is at least 0.01 wt. %, but can vary from about 0.01 to about 1 wt. % of the inhibitor.

Without wishing to be bound by any one particular theory, it appears that compounds such as (IVA) inhibit thermal decomposition by the following mechanism. It is first assumed that thermal decomposition of the nitroso compounds is triggered by cleavage of the nitroso group giving nitrous oxide (as evidenced by the evolution of a brown gas upon exposure to air). The nitrous oxide then catalyzes the further decomposition of the nitrosated inhibitor compound. One possible route for this further decomposition is the nitrous oxide induced cleavage of another nitrous oxide (autocatalysis).

Nitrous oxide is known to react with any primary or secondary amines such as phenylenediamines. Thus if a phenylenediamine is present when nitrous oxide is formed, then the nitrous oxide will react with the amine and not be available to induce further cleavage of the nitroso compounds. However, phenylenediamines are not the only compounds with which the nitrous oxide can react. The phenolic compounds (structures V and VI) mentioned above can also react with the nitrous oxide.

The mixture of inhibitor and stabilizer is used to prevent the polymerization of vinyl aromatic compounds during their distillation. Vinyl aromatic compounds to which this mixture can be added include but are not limited to styrene, alpha-methyl styrene, divinylbenzene, vinyl toluene, vinyl naphthalene and polyvinylbenzene. An effective amount of the mixture is that amount which will give from about 1 to about 10,000 ppm of the inhibitor.

Having added the effective amount of inhibitor plus stabilizer to the feed containing the vinyl aromatic compound, the feed is distilled at a temperature of about 65° C. to about 150° C. in standard distillation column. The distillation temperature can be controlled by adjusting the pressure in the column from about 0 kPa (0 psi) to about 165 Pa (24 psi) absolute. Further, the inhibitor and stabilizer mixture may be added to the vinyl aromatic compound in any convenient manner. Usually the mixture is added in liquid form by periodically or continuously adding the required amount to the inlet distillation feed. In this respect, if the inhibitor and/or stabilizer are solids, they are dissolved in an appropriate solvent. Illustrative of the solvents which can be used are the vinyl monomer itself, toluene, benzene, ethylbenzene, xylene, etc., and mixtures thereof. The preferred solvent is ethylbenzene which allows for easy separation from the purified vinyl aromatic compound.

The following examples are presented in illustration of the invention and are not intended as undue limitations in the generally broad scope of the invention as set out in the appended claims.

EXAMPLE 1

In a 3 L round bottom flask, there were placed 500 g of N,N'-di-2-butyl-1,4-diaminobenzene obtained from UOP and identified as UOP No. 5® and 700 g of hexanol. To this flask, which was held at a temperature between 20° C. and 40° C., there were added 460 g of concentrated hydrochloric acid (36 wt. % aqueous) drop-wise over a one-hour period. After this addition, the mixture was stirred for 10 minutes and then 325 g of sodium nitrite was added over a one-hour period while again maintaining the temperature between 20° C. and 40° C. After the addition was completed, the reaction mixture was neutralized to pH 7 by the addition of 84 g of sodium bicarbonate, which results in a dark brownish slurry. The slurry was filtered and the resulting solid product was washed with water and then ethanol to give an off-white to yellow crystalline solid identified as sample A.

EXAMPLE 2

The onset of decomposition of sample A (N,N'-di-2-butyl-N,N'-dinitroso-1,4-diaminobenzene) and sample A plus 100 ppm wt. of N,N'-di-2-butyl-1,4-diaminobenzene (sample B) were measured by heating on a heating block and visually observing the decomposition onset and by thermogravimetric analysis. The results are presented below.

| Sample I.D. | Decomposition Onset (° C.) by Heating Block | Decomposition Onset by TGA* Analysis | |
| --- | --- | --- | --- |
| | | Air | $N_2$ |
| A | 128° | 155 | 157 |
| B | 150° | 174 | 160 |

*TGA is a thermal gravimetric analysis

We claim as our invention:

1. A process for increasing the thermal stability of a polymerization inhibitor selected from the group consisting of

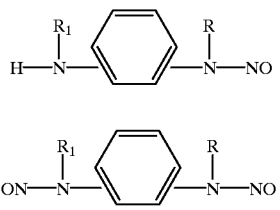

(I)

(II)

and mixtures thereof, where R and $R_1$ are each independently hydrogen, cyclohexyl, phenyl or an alkyl group having from 1 to 18 carbon atoms, the process comprising adding to the organic compound an effective amount of a stabilizer selected from the group consisting of (IV)

(V)

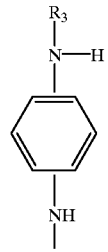

(VI)

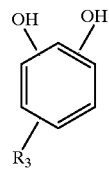

and mixtures thereof, where $R_2$ is selected from the group consisting of hydrogen, cyclohexyl, phenyl, and an alkyl group having from 1 to 10 carbon atoms, and $R_3$ is selected from the group consisting of hydrogen, cyclohexyl, an alkyl group having from 1 to 18 carbon atoms and an aromatic group having from 6 to 10 carbon atoms.

2. The process of claim 1 where the polymerization inhibitor has structure (II) and the stabilizer compound has structure (IV).

3. The process of claim 2 where the polymerization inhibitor is N,N'-dinitroso, N,N'-di-2-butyl-p-phenylenediamine and the stabilizer compound has structure (IV).

4. The process of claim 3 where the stabilizer is N,N'-di-2-butyl-1,4-diaminobenzene.

5. The process of claim 1 where the stabilizer is present in the mixture in an amount from about 0.0001 wt. % to about 1 wt. % of the inhibitor.

6. A process for inhibiting the polymerization of a vinyl aromatic compound during the distillation of the vinyl aromatic compound comprising adding to the compound an effective amount of a mixture of at least one polymerization inhibitor and at least one stabilizer, where the inhibitor is selected from the group consisting of:

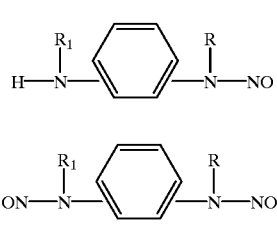

(I)

(II)

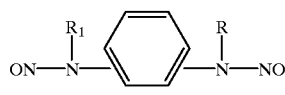

and mixtures thereof, where R and $R_1$ are each independently hydrogen, cyclohexyl, phenyl or an alkyl group having from 1 to 18 carbon atoms, and the stabilizer is selected from the group consisting of (IV)

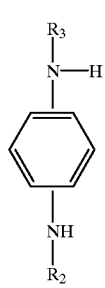

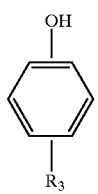
(V)

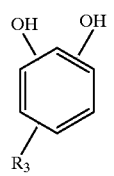
(VI)

and mixtures thereof, where $R_2$ is selected from the group consisting of hydrogen, cyclohexyl, phenyl, and an alkyl group having from 1 to 10 carbon atoms, and $R_3$ is selected from the group consisting of hydrogen, cyclohexyl, an alkyl group having from 1 to 18 carbon atoms and an aromatic group having from 6 to 10 carbon atoms.

7. The process of claim 6 where the inhibitor is present in an amount from about 0.0001 to 1 wt. %.

8. The process of claim 6 where the polymerization inhibitor is a mixture of compounds having structures (I) and (II).

9. The process of claim 6 where the polymerization inhibitor has structure II and the stabilizer compound has structure (IV).

10. The process of claim 6 where the polymerization inhibitor is N-N'-di-2-butyl-N,N'-dinitroso-1,4-diaminobenzene and the stabilizer compound has structure (IV).

11. The process of claim 6 where the stabilizer is N,N'-di-2-butyl-1,4-diaminobenzene.

12. The process of claim 6 where the mixture contains from about 0.01 to about 1 wt. % of stabilizer.

13. The process of claim 6 where the vinyl aromatic compound is selected from the group consisting of styrene, alpha-methyl styrene, divinylbenzene, vinyl toluene, vinyl naphthalene, and polyvinyl-benzene.

* * * * *